United States Patent [19]

Augspurger et al.

[11] Patent Number: 5,300,438
[45] Date of Patent: Apr. 5, 1994

[54] COMPOSTING APPARATUS

[75] Inventors: Quent Augspurger; Charles H. Bartlett, both of Phoenix, Ariz.

[73] Assignee: Augspurger Engineering, Phoenix, Ariz.

[21] Appl. No.: 908,367

[22] Filed: Jul. 6, 1992

[51] Int. Cl.⁵ .................... C12M 1/10; C12M 1/02
[52] U.S. Cl. .................... 435/312; 435/315; 435/316; 422/184; 422/209; 366/220; 366/227; 366/228
[58] Field of Search ............. 435/299, 303, 311, 312, 435/313, 315, 316, 813; 422/184, 209, 210; 366/105, 219, 220, 225, 226, 227, 228, 232, 233, 144, 145, 147, 149; 71/8, 9, 10, 11, 14; 34/108, 126, 130, 132, 133 H

[56] References Cited

U.S. PATENT DOCUMENTS

| | | | |
|---|---|---|---|
| 110,482 | 12/1870 | Marshall | 366/228 |
| 328,938 | 10/1885 | Hassenpflug | 366/228 |
| 3,178,267 | 4/1965 | Larson | 71/9 |
| 3,245,759 | 4/1966 | Eweson | 435/312 |
| 3,930,799 | 1/1976 | Eweson | 422/184 |
| 4,756,623 | 7/1988 | Bishop | 366/233 |

FOREIGN PATENT DOCUMENTS

| | | | |
|---|---|---|---|
| 3206617 | 9/1983 | Fed. Rep. of Germany | 435/287 |
| 2550420 | 2/1985 | France | 435/299 |
| 2598705 | 11/1987 | France | 435/312 |

*Primary Examiner*—Michael G. Wityshyn
*Assistant Examiner*—William H. Beisner
*Attorney, Agent, or Firm*—Gregory J. Nelson

[57] ABSTRACT

A composting apparatus and method utilizing a vessel for receiving organic material which is rotatably supported. In a preferred embodiment, the vessel has a corrugated body to move and agitate the material. In another embodiment, the vessel is fabricated from large containers, such as refuse containers, secured end-to-end at their top ends. The vessel is rotated by a drive wheel engaging a peripheral track on the exterior of the vessel.

11 Claims, 5 Drawing Sheets

COMPOSTING APPARATUS

BACKGROUND OF THE INVENTION

1. Field of the Invention

The present invention relates to an apparatus and method for the decomposition of organic materials such as yard waste, waste paper and the like.

For many years, it has been common practice for gardeners to make compost from leaves, grass clippings, food waste and the like. The material is generally placed in a pile or in a compost bin which is then periodically agitated and over a period of time the inorganic material will naturally decompose becoming converted into a nutrient rich humus. The resulting humus material is extremely beneficial to gardeners as the material can be mixed with soil or spread over the existing soil to provide a protective plant covering, reducing evaporation and protecting plants from heat and cold and also enhances the existing soil. The compost covering also promotes germination of seeds and plants. Composting is attractive to gardeners for these benefits and further because composting reduces the volume of household waste that is deposited into landfills.

Composting basically is a controlled biological decomposition of organic material under aerobic conditions. The process relies on naturally occurring microorganisms, mainly bacteria and fungi, to break down organic compounds into simpler substances.

2. Description of Related Art

Several methods of composting are used today, either on a small scale basis by individuals or in larger operations where commercial operators and municipalities conduct waste management facilities. One common method of composting is termed the "windrow" method in which compostable material is simply placed in windrows. The windrows are periodically turned to increase the exposure to oxygen. In addition, the windrows may be watered periodically to maintain a predetermined moisture content for proper decomposition conditions. This method is more widely practiced in Europe.

Various modified forms of the windrowing method may also be found. In some applications, the compostable material is simply placed in piles and covered. The material may be wetted and bacteria added. Aeration is accomplished by introducing oxygen to the compost piles through a distribution system.

As an alternative to the windrow or static aeration methods of composting, in-vessel composting is also known. In-vessel composting devices offer some advantages including better process control, higher rate decomposition and better odor control. Odor control is a major concern of composting systems. Various in-vessel composting and other type units and other systems can be found in the prior art patents.

U.S. Pat. No. 2,699,629 shows a device for mulching vegetable plants in which organic refuse material such as garbage, manure, dried leaves, grass clippings and other materials are placed in a water suspension to cause mechanical disintegration. The free-flowing pulp mixture is then sprayed to provide an insulating protective area covering the soil surrounding the plant and to retain moisture therein.

U.S. Pat. No. 3,269,824 discloses a soil conditioning pellet which consists essentially of a carrier of re-pulped and compressed waste paper fiber along with a mixture of soil fertilizing ingredients absorbed therein.

U.S. Pat. No. 3,942,769 discloses a composting unit comprising a container mounted in an elevated position for rotation about a substantially horizontal axis. A door is provided in the container through which the material to be composted can be loaded into the container. The drum or container is manually rotated periodically.

U.S. Pat. No. 4,067,140 discloses a method of making mulch in which finely divided fibers of paper are coated with a mixture of a solvent or carrier such as water, a wetting agent and a dye. The finely divided fibers of paper are contacted with the mixture by tumbling in a drum.

While the above-described apparatus and methods for composting and for the utilization and decomposition of waste paper are known, such apparatus and methods have not gained large acceptance by the individual homeowner for various reasons. The prior systems generally require substantial attention, as for example, the homeowner must periodically turn the material manually in a drum. The devices found in the prior art also often emit objectionable odors and attract flies and other insects.

SUMMARY OF THE INVENTION

Thus, there exists a need for a simple, effective and highly efficient composting system which may be utilized both by the individual gardener or homeowner and also which may be used on a larger scale for municipal and commercial waste treatment systems.

Briefly, the present invention comprehends a composter for residential and commercial use having a vessel which is rotatably mounted. The vessel receives the organic material and bacteria and water as required. In one embodiment, the vessel is formed from a corrugated pipe so the corrugations move the material along through the vessel. In another embodiment, the vessel is formed from large commercial refuse containers made of a material such as polyethylene. The containers are joined at their open ends in end-to-end fashion. A motorized drive wheel engages a circumferentially extending track.

BRIEF DESCRIPTION OF THE DRAWINGS

The above and other objects of the present invention will be more fully appreciated from the following description, claims and drawings in which:

DESCRIPTION OF THE PREFERRED EMBODIMENTS

Figures 10, 19:
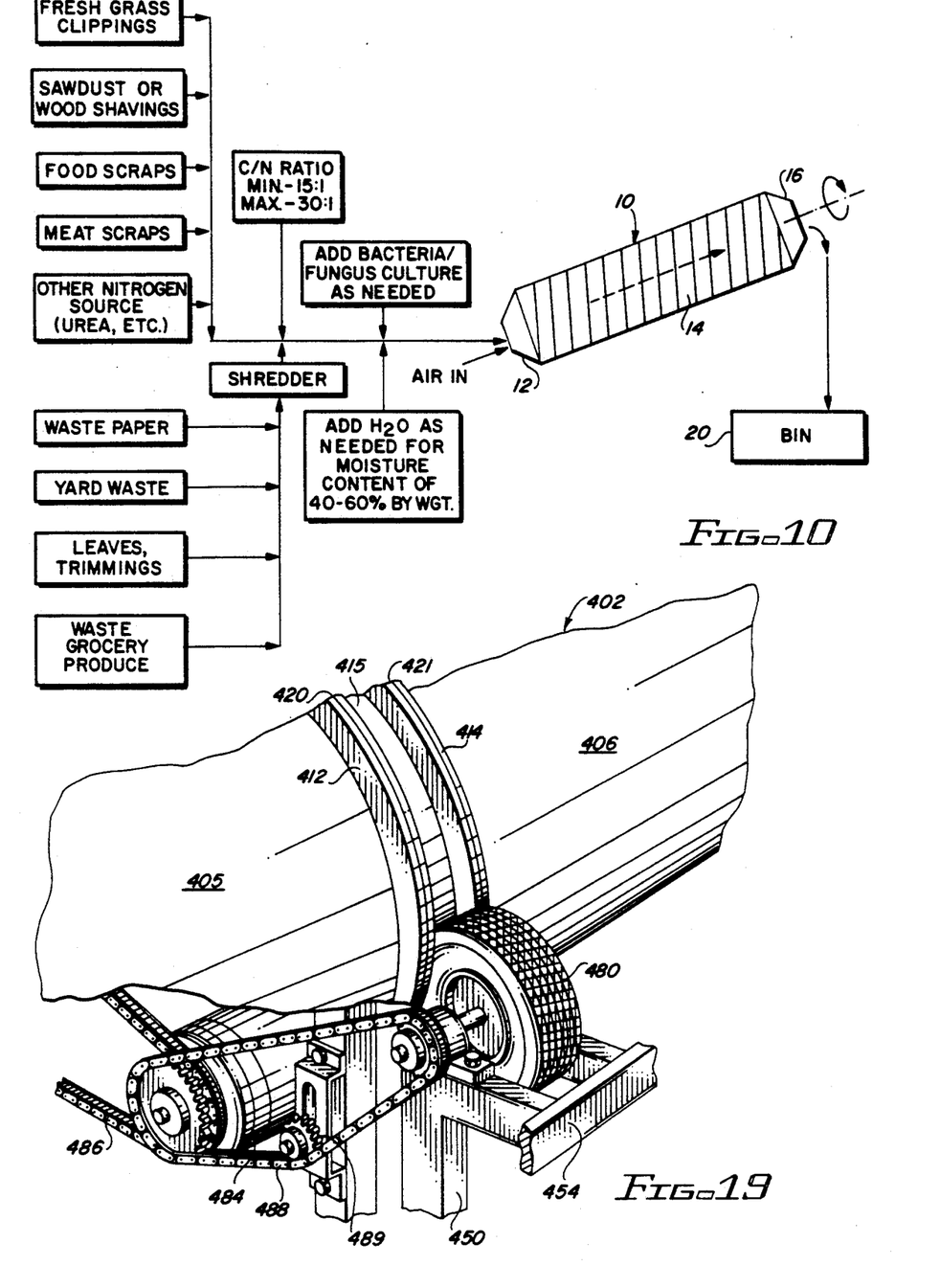
FIG. 10 is a schematic diagram illustrating the composting process carried out by the apparatus as shown in FIGS. 1 to 9.
FIG. 19 is a detail view of the drive arrangement of FIG. 18.

Turning now to the drawings, FIG. 10 illustrates in schematic form a representative composting process as carried out by the various embodiments of the present invention. The composting device, as will be more fully described hereafter, is generally designated by the numeral 10. The composting device has an inlet 12 with a chamber 14 into which material to be composted is charged. The inlet also permits air to enter into the composting chamber 14 inasmuch as composting is an aerobic process. Although the diagram is shown with reference to the apparatus of FIG. 1, the schematic diagram is representative of the process carried out by the various embodiments of the invention described herein.

As indicated in FIG. 10, a variety of organic materials may be used as starting materials for composting which are broken down into more simple substances for gardening and similar uses. These materials indicated may consist of wood shavings, yard waste, food scraps and the like. Additional nitrogen may be added as indicated with the preferred carbon-to-nitrogen ratio being between 15-1 to 30-1. Various nitrogen sources may be utilized such as nitrogen containing fertilizer, urea and the like. Bacteria or fungus cultures may also be added to accelerate the process. It is also desirable to add water to the compost materials to maintain moisture content of approximately 40% to 60% by weight.

A primary source of compost material is waste paper, primarily newsprint. Newsprint can be a valuable source of composting material and it is preferable to first shred the material to reduce composting time. Yard waste, leaves and waste food may also be used as a starting material and also may be first shredded as indicated prior to introduction into the composter 10. Over a period of time, aerobic decomposition proceeds and the resulting composting material is discharged at the outlet 16 of the composter and delivered to a bin 20 for subsequent use such as application to a garden or to be mixed with soil.

Turning to the drawings, particularly FIGS. 1 through 9, a preferred embodiment of the composter of the present invention is shown as has been indicated above and is generally designated by the numeral 10. The composter is shown having a generally elongate cylindrical body 22 which defines composting chamber 14. The cylindrical body 22 is formed having a plurality of helical convolutions 24 which extend continuously from the lower inlet end to the upper outlet end. A particularly convenient construction is the utilization of a large corrugated pipe such as a culvert for the body 22. The discharge end 16 is provided with a truncated conical cap having an end surface 25 which defines an opening 28 through which the compost may be discharged into a receiving bin 20 or other receptacle. The inlet end 12 is also provided with a generally conical cap 32 which is truncated having a surface 34 which defines an inlet opening 36 through which material to be composted is introduced into the internal composting chamber 14. A circular door 38 has a hinge 44 at one side and a latch mechanism 46 at the opposite side so the door can be unlatched and swung upwardly to provide access to the composting chamber 14.

Figure 3:
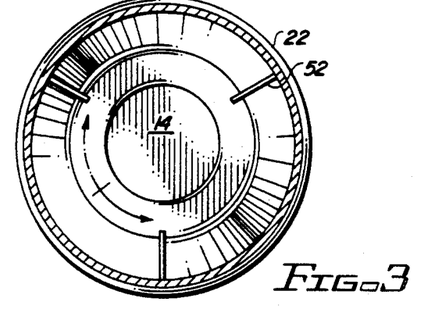
FIG. 3 is a sectional view taken along line 3—3 of FIG. 1.

The internal walls of the cylindrical chamber 14 are provided with a plurality of longitudinally extending baffles 50 which are shown as sections of angle iron having a flange 52 extending radially into the chamber. Preferably the baffles extend substantially the entire length of the composting chamber 14 or are segmented and overlapped to effectively extend the full length of the chamber so that material is urged from the inlet end to the outlet end by the combined action of the helical convolutions 24 and the baffles 50. FIG. 3 illustrates the typical arrangement for the baffles about the interior periphery of the body 22 with three equally-spaced baffles being shown.

The composter 10 is preferably positioned for operation in a slightly elevated position with the discharge end elevated approximately 20°. The length of the chamber and inclination will determine the residence time which may vary with the make-up of the starting material, available nitrogen, moisture and other process factors. The device may be positioned on a stationary base but for convenience of operation, preferably has a mobile frame with longitudinally extending side frame members 56 and transverse frame members 58 extending between the longitudinal members. Wheel assemblies 60 are provided at opposite sides of the frame disposed towards the outlet end. An adjustable jack stand 62 is provided at the opposite end of the frame to adjustably support the unit. This allows the device to be transported to a use-site and then leveled.

Figures 1, 2:
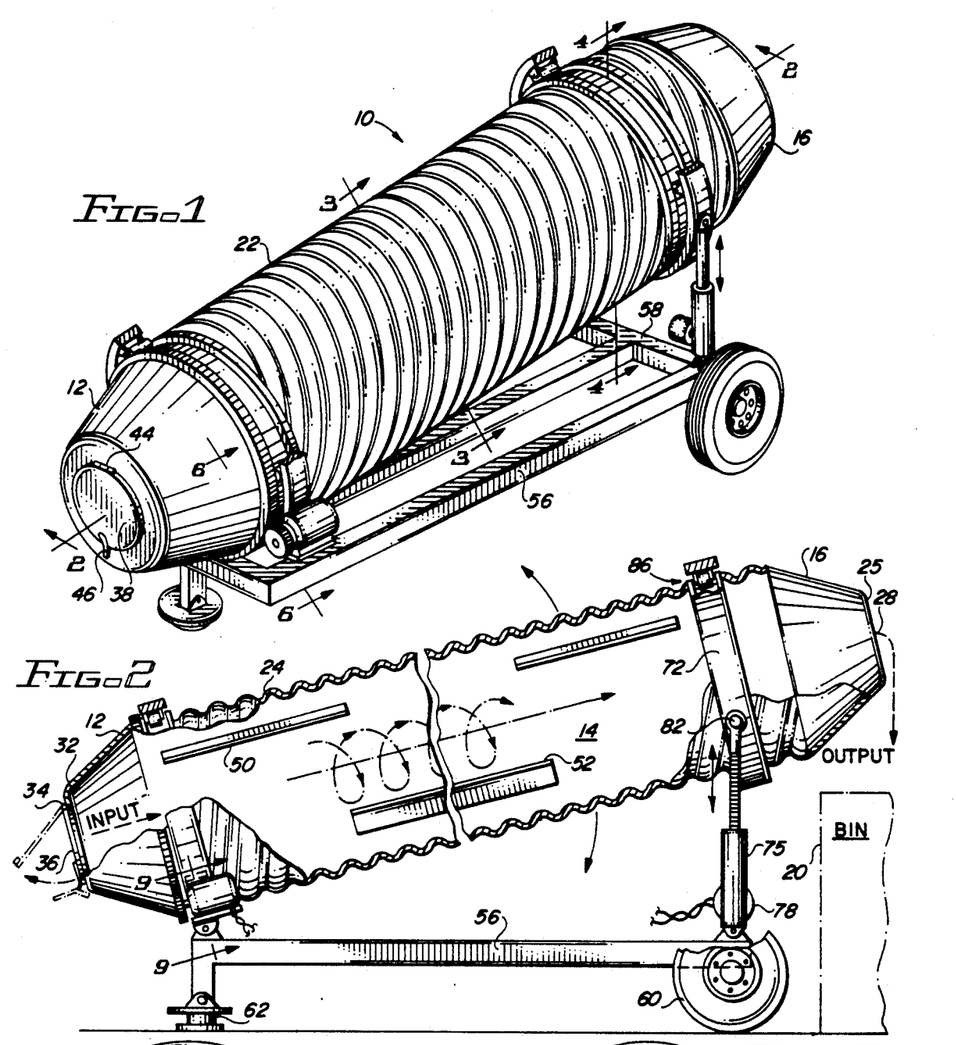
FIG. 1 is a perspective view of one embodiment of the composting apparatus of the present invention.
FIG. 2 is a sectional view taken along line 2—2 of FIG. 1.
Figures 4, 5, 7, 8, 16:
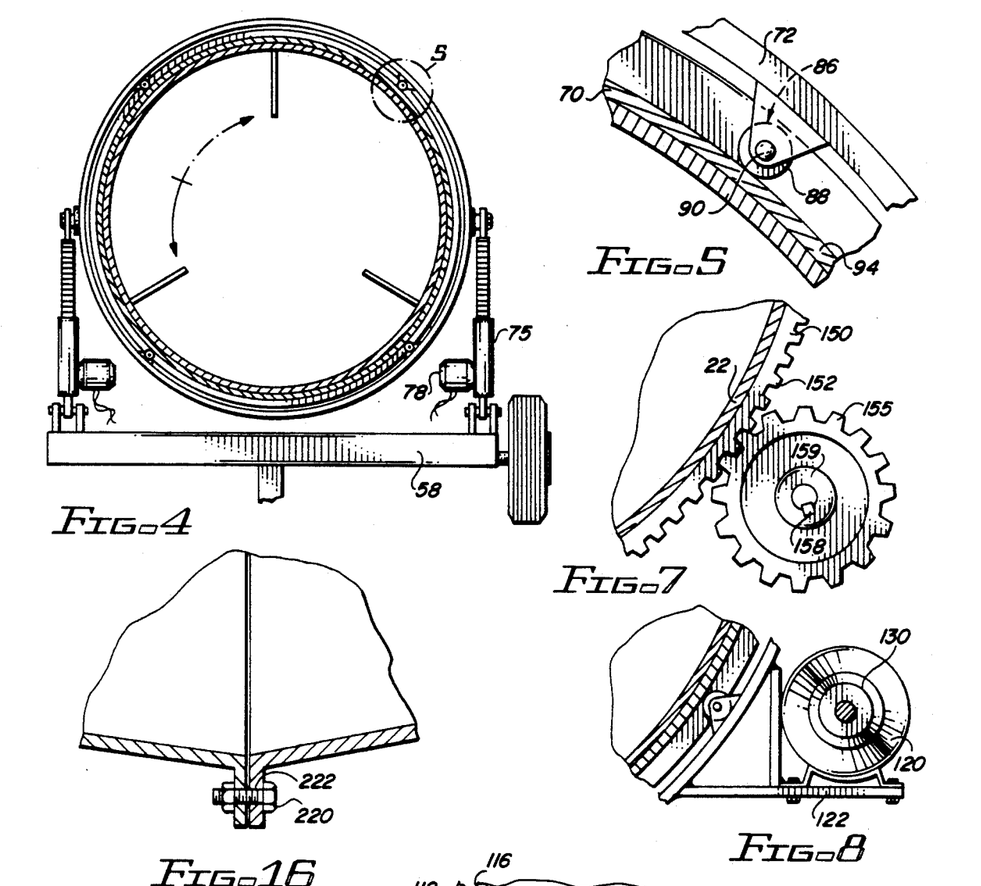
FIG. 4 is a sectional view taken along line 4—4 of FIG. 1.
FIG. 5 is a detail view of a portion of the roller and track assembly as indicated in FIG. 4.
FIG. 7 is a detail view illustrating an alternate drive arrangement for the composting drums.
FIG. 8 is a detail view of the motor mounting and track.
FIG. 16 is a detail view of the joint interconnecting the container sections.
Figure 6:
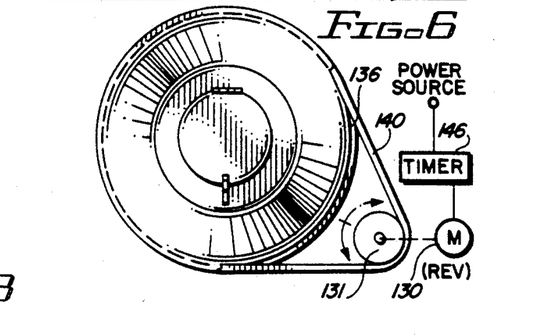
FIG. 6 is a sectional view taken along lines 6—6 of FIG. 1.

The discharge end of the composter is supported for rotation as best seen in FIGS. 2, 4 and 5. Generally a flat band-like track 70 extends circumferentially about the body 22 of the composter adjacent the outlet end. Circular roller support band 72 extends circumferentially about the body of the composter spaced apart from the track 70. The roller support band is attached to actuators 75 vertically extending from the frame at opposite sides of the composter body. The actuators 75 may be hydraulic members or may be, as shown, screw jack members electrically operated by motor 78 which will selectively raise or lower the discharge end of the composter. The upper end of the jacks are pivotally attached at 82 to the exterior of the roller support band 72.

The roller support band carries a plurality of roller assemblies 86. The roller assemblies each have a roller 88 carried on axle 90. The rollers engage the exterior of the track 70. The position and spacing of the roller assemblies may vary with, as shown in FIG. 4, four equally spaced-apart assemblies being typical. To maintain the rollers on the track, the edges of the track are provided with upstanding flanges 94 which are closely spaced from the opposite sides of the rollers to maintain the proper alignment.

Figures 9, 17:
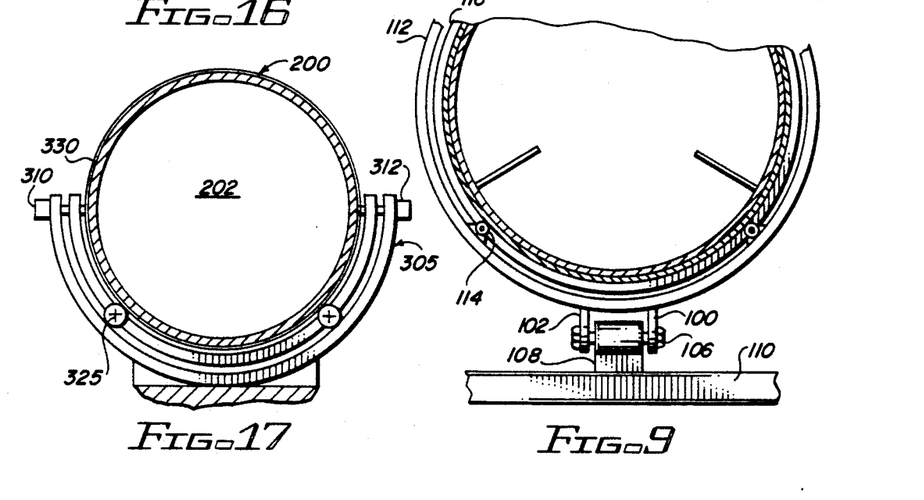
FIG. 9 is a sectional view taken along line 9—9 of FIG. 2.
FIG. 17 is a cross sectional view illustrating an optional trunnion mounting for a tilting axis of the device shown in FIG. 11.

The lower or inlet end 12 of the composter is pivotally mounted on the frame as seen in FIG. 9 to accommodate varying the inclination of the composter. A pair of spaced-apart flanges 100 and 102 extend downwardly from support band 112 to receive transversely-extending axle 106 which is carried on axle support 108 centrally mounted on the transverse main frame member 110. The pivot assembly supports circular roller support rim 112 which carries a of roller members 114 which engage track 116 which extends circumferentially at the inlet end of the composter body 22. The circumferential track is provided with upstanding flanges which are closely spaced from the sides of the rollers 114 to maintain the rollers on the track.

As indicated above, the composting process is enhanced if the contents are periodically or perhaps even continuously tumbled or agitated. Further, with the device as shown, the baffles and helical convolutions will cause the material to advance from the input end to the output end of the composter as rotation occurs.

To impart rotation to the composter, drive motor 130 is mounted on a platform 122 which projects from the roller support rim 112. The output shaft of the drive motor 130 carries a pulley 131. The details of the motor mounting is best seen in FIGS. 1, 2, 6 and 8. A belt track 136 extends peripherally about the lower end of the body 22 of the composter disposed adjacent the lower roller track. The belt track may be an elastomeric material which has suitable frictional characteristics or may include a plurality of teeth or projections. Drive belt 140 extends about the belt track 136 and pulley 131 and upon energization of the motor 130, will cause the composter body to rotate at a predetermined rate of rotation, generally in the range of ½ to 2 rpm. Preferably the motor has a motor control which includes a timer 146 which may be adjusted to periodically turn the motor on and off as determined by the process requirements. The motor 130 may be a reversing motor as in some applications, periodic reversal will enhance mixing of the contents.

In use, the composter of the present invention is mobile and may be transported to a use site on the mobile trailer frame and erected and leveled at stand 62. The discharge end of the composter is elevated to the desired position by the screw jack 75. A bin 20 is placed beneath the discharge end to receive the compost material. The compost material, of the type shown in FIG. 10, is charged into the device along with moisture, nitrogen and bacteria or fungus cultures if required. The materials are charged through inlet door 46 and the composting process will begin. Periodically, the device is rotated by motor 130 under the control of timer 146. As rotation occurs, the compost material will slowly advance from the input to the discharge end. The rotation time is selected so that by the time the material reaches the discharge port 28, the composting process is complete and digested material ready for use is discharged into bin 20.

FIG. 7 shows an alternative drive arrangement for the composter body in which a peripheral ring gear 150 is secured about the composter body 22 having a plurality of teeth 152 which are in engagement with the teeth of drive gear 155 which is secured to the output shaft 159 of a motor by a suitable key 158. The large gear ratio will cause the composter to turn at a low predetermined rate.

The composting device described with reference to FIGS. 1 to 9 works particularly well in operations where composting is continuous or larger quantities of compost are encountered such as in municipal waste composting facilities. For smaller operations and for individual homeowners, an alternate embodiment of the invention may be preferred and is illustrated in FIGS. 11 to 17. The composter of this embodiment is generally designated by the numeral 200 and has a drum 201 which encloses the composting chamber 202 having internal helical flights 205. The drum is shown as having the greatest diameter at the midpoint and oppositely tapers to end walls 206, 208. See FIG. 12. The drum is preferably fabricated from two large, generally frustroconical containers such as trash containers of the type roto-molded or roto-cast from polyethylene or similar material. The containers are positioned in top-to-top arrangement with flange 212 of one container abutting the flange 214 of the other as best shown in FIG. 16. The flanges are secured together by fasteners such as bolts 220 placed in bores 222 at spaced-apart peripheral locations. The abutting flanges may be sealed with a gasket or a suitable sealant but it is preferred that the flanges at the interface be simply bolted together as this construction will allow some leakage so that excess liquid can drain from the container.

Figures 11, 12, 13, 14, 15:
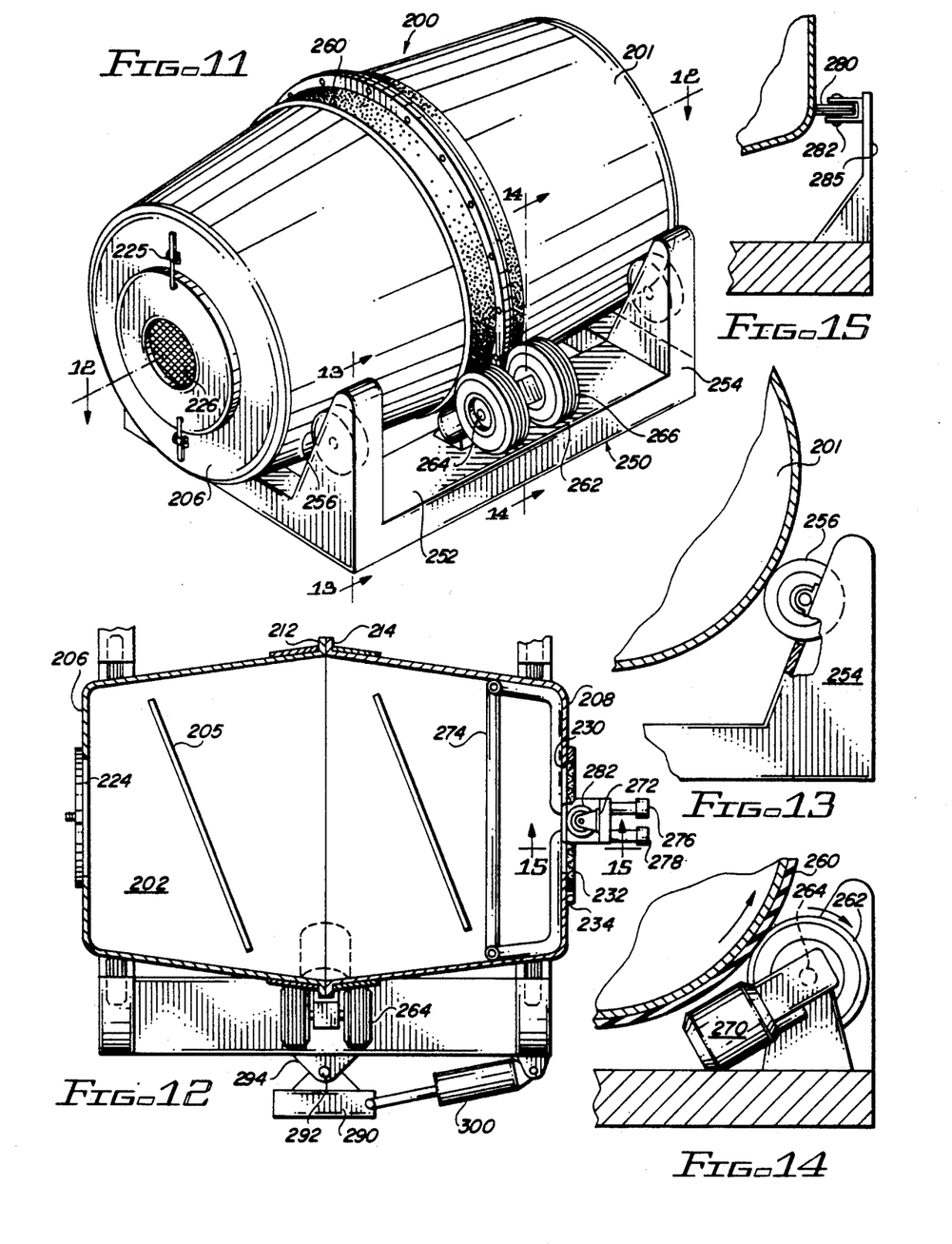
FIG. 11 is a perspective view of an alternate embodiment of the composting apparatus of the present invention.
FIG. 12 is a sectional view taken along line 12—12 of FIG. 11.
FIG. 13 is a sectional view taken along line 13—13 of FIG. 11.
FIG. 14 is a sectional view taken along line 14-14 of FIG. 11.
FIG. 15 is a sectional view taken along line 15—15 of FIG. 12.

The inlet end wall 206 defines an opening to compartment 202. The opening is provided with a generally circular door 224 which is secured in place by toggle clamps 225 and which includes a screened opening 226. A removable funnel, not shown, may be inserted into the opening to facilitate loading.

The end wall 208 at the discharge end of the unit also defines an opening 230 which is covered by screen 232 which is secured to the end wall 208 by a hinge 234. Screen 232 allows admission of air and will keep flies and insects from entering and leaving the compartment 202.

The container is mounted for rotation on a base 250. The base 250 has a frame 252 which is generally rectangular having upstanding posts 254 at the corners of the frame. Each of the posts 254 carries a roller 256 which engages the exterior surface of the container to support the container for rotation.

Positioned on opposite sides of the mating flanges at the middle of the container are a pair of frictional strips 260 which extend circumferentially around the container. Drive wheels 262 are mounted on a common axis 264 each having a solid or pneumatic rubber tire 266 which engages one of the frictional circumferential strips 260. A gear motor 270 drives axle 264 and wheel assembly at a predetermined speed. As shown in FIG. 14, the frictional engagement between the drive wheel assembly and the frictional strips will cause the entire container to rotate at a predetermined speed supported on rollers 256. The gear motor 270 may be selectively operated through a timer circuit to rotate at predetermined times.

The container is restrained from longitudinal movement by idler wheels 280 which are horizontally mounted on a generally vertical axle 282, as seen in FIG. 15. The axles 282 are supported at opposite ends of the base 250. The idler wheels engage the opposite end walls of the container at locations adjacent the peripheral edge of the side wall.

The entire base 250 is pivotally supported on a pedestal 290 which has a horizontal, generally transversely extending pivot shaft 292 which engages member 294 at the underside of the base at the approximate midpoint of the container. With this arrangement, the container and base may tilt end-to-end in either direction. The tilting accommodates loading during which the inlet end is elevated. During unloading the discharge end is lowered. During compost digesting, an inclination is selected to provide the proper residence or through-put time. To control the tilting motion, a hydraulic actuator or screw 300 has a cylinder body with its rod end pivotally connected to the pedestal and the body pivotally connected to the base so that selective extension and retraction of the actuator will impart the desired tilting motion to the base and container.

A rotatable coupling 272 is located at the center of the door at the discharge end. The couplings are attached to a heat exchange element 274 positioned in the chamber 202 through which a heat exchange fluid may be circulated. Externally the couplings are attached to conduits 276, 278. A cold fluid may be introduced to element 274 via conduit 276 and discharged via conduit 278 to cool the contents of the composter and maintain a predetermined temperature. Alternatively, the heat exchanger may be used to heat the contents to kill pathogens and other undesirable constituents of the compost such as weed seeds.

In other respects, the compost device operates as has been described above with reference to FIGS. 1 to 9. The material to be composted is loaded into the chamber 202 through the opening in end wall 206. The device is tilted to the desired inclination and drive motor 270 energized to cause the container to periodically rotate. The internal helical flights 205 extend about the interior of the drum to urge compost material from the inlet to the outlet end. When composting is complete, the material may be discharged or removed at access opening 232. Excess liquid is permitted to drain from the unit at the interface of the flanges at the midpoint of the drum. When not in use, the drum may be entirely lifted from the base as the drum simply rests on the drive and idler rollers.

FIG. 17 shows an alternate support arrangement for the compost drum 200. In this embodiment, an outer, generally semi-circular cradle 305 is provided which is oppositely supported for tilting movement along trunnion axis 310 by stub shaft members 312. A semi-circular frame support is disposed between the outer support and the drum. The frame support carries a pair of rollers or wheels 325 at locations equi-distance from the trunnion axis. One or more of the rollers is driven by a gear motor or similar drive unit. Preferably the exterior of the container is provided with a frictional strip 330 which extends circumferentially around the drum as engaged by the rollers. The trunnion axis will permit tilting of the drum to the desired angle.

Figure 18:
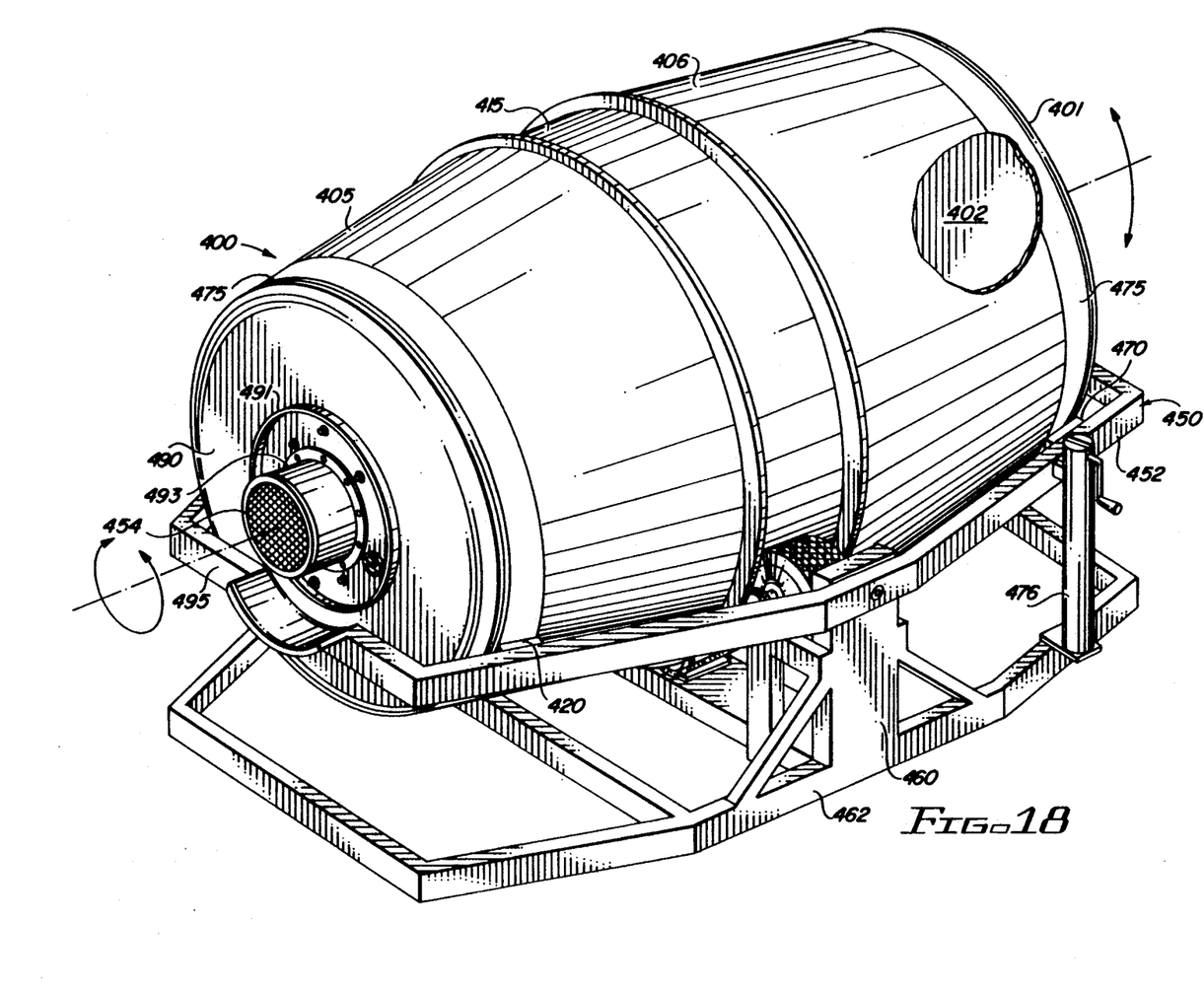
FIG. 18 is a perspective view of an alternate drum and drive arrangement.

Still another embodiment of the present invention is shown in FIGS. 18 and 19 and is generally designated by the numeral 400. Embodiment 400 has a housing 401 which encloses a composting chamber 402. The housing is similar to that shown in FIGS. 11 to 17 and is fabricated from two generally frustro-conical sections which are shown as containers such as large trash containers. The containers 405, 406 are positioned in top-to-top relationship. A track 415 is interposed between the containers. The track has a circular surface and opposite circular flanges 420 and 421 which are respectively secured to the flanges 412 and 414 of the containers. The end walls of the containers define openings, not shown, for charging and discharging material. Discharge end wall 490 is shown having access hatch 491. Hatch 491 has an annular chute 493 secured thereto. A removable screen 495 extends across the end of the chute. The decomposed material is discharged through the chute preferably with the housing rotating to assist in material removal. The screen 495 classifies the material and screens of selected sizes may be used.

The container is mounted for rotation on a frame 450 which has side members 452 and end members 454. The frame is oppositely supported on a pair of vertically extending posts 460 transversely located on a base frame or plate. Bearing surfaces 470 which may be rollers, are located at the inner opposite ends of the frame and engage annular wear bands 475 positioned at the opposite ends of the drum. The frame may be tilted by manually actuated jack stand 476.

Rotation of the drum is imparted by a pair of drive wheels 480 mounted on opposite sides of the frame. Each of the drive wheels is a solid or pneumatic rubber tire which engages the circumferential track. A gear motor 484 is located on the base beneath the drum and is in driving engagement with the drive wheels by means of chain drives 486 and 488. An appropriate idler or chain tightener 489 may be associated with each of the chains. The gear motor is selectively operated through a timer circuit to rotate at a predetermined time periods. The advantage of the embodiment 400 is that the drive wheels 480 engage the metal band 415 so as not to impart excessive wear to the softer, synthetic material of the housing.

In order to test the effectiveness of the composter of the present invention, a composter was constructed according to the above teachings generally as shown in FIGS. 11 through 14. The composter was charged with the following materials: Shredded trimmings from carob trees and operated under the following conditions: Moisture content was held between 40% to 60% by weight. The container was rotated each day approximately five to 10 revolutions. Ammonium sulphate was added during the third week to provide additional nitrogen.

Compost suitable for gardening use was produced in approximately 30 days, substantially free of problems with odors or insects.

It will be obvious to those skilled in the art to make various changes, alterations and modifications to the composting method and apparatus described herein. To the extent such changes, alterations and modifications do not depart from the spirit and scope of the appended claims, they are intended to be encompassed therein.

We claim:

1. An apparatus for receiving and decomposing organic materials and discharging a compost, said apparatus comprising:
   (a) a body having a wall with exterior and interior surfaces defining a decomposition chamber, said body being fabricated from a section of corrugated metal pipe of the type having helical corrugations extending around the exterior and interior wall surfaces of the pipe, said body having an inlet at one end and an outlet at the opposite end;
   (b) a frame having support means for rotatively supporting said body thereon;

(c) drive means including motor means for rotating said body in a predetermined rotational direction and at a predetermined rotational speed;
(d) elevation means for selectively positioning said body in a predetermined position to control residence time within the decomposition chamber and to accommodate loading and unloading; and
(e) baffles extending axially along the internal wall of the decomposition chamber which baffles, along with the interior helical corrugations, will mix the organic material and move the material between the inlet to the outlet as the body rotates at a predetermined speed and rotational direction as decomposition occurs.

2. The apparatus of claim 1 wherein at least one of said inlet and outlet is provided with openings for admission of air into the decomposition chamber.

3. The apparatus of claim 1 further including heat exchange means extending into said decomposition chamber for circulating a heat exchange fluid through the said chamber to control the temperature within said chamber.

4. The apparatus of claim 1 wherein said inlet and outlet are truncated conical members and wherein said inlet is provided with a latched door.

5. An apparatus for receiving and decomposing organic material and discharging a compost, said apparatus comprising:
(a) a body defining a decomposition chamber having baffles therein, said body being comprised of a pair of synthetic containers, each container having a bottom wall, a side wall and each having an open upper end defined by a flange extending peripherally about the upper edge of the side wall, said containers being disposed in open-end-to-open-end relationship and having an annular channel member disposed therebetween to permit controlled leakage from the decomposition chamber, said channel member having flanges engaging the respective flanges of each of said containers and providing rigidity to the body, said body having an outlet at one end;
(b) a base including a cradle and roller means for supporting said body for rotation;
(c) drive means for rotating said body including a pair of friction wheels engaging the said channel member at locations on opposite sides of a vertical axis through said body with at least one of said wheels being driven by a motor; and
(d) elevation means for selectively positioning said cradle and body in a predetermined position to control residence time within the decomposition chamber and accommodate loading and unloading.

6. The apparatus of claim 5 further including timer means for selectively controlling the operation of the said drive means.

7. The apparatus of claim 5 further including heat exchanger means extending into said decomposition chamber for circulating a heat exchange fluid therethrough to control the temperature in the said decomposition chamber.

8. The apparatus of claim 5 wherein said baffles are positioned in said decomposition chamber to mix and move organic material from the inlet to the outlet as decomposition occurs.

9. The apparatus of claim 5 wherein said cradle includes bearing means engaging said body for rotational movement.

10. The apparatus of claim 5 further including classifier means associated with said outlet for classifying the organic material as it is discharged from the rotating body.

11. The apparatus of claim 10 wherein said classifier means comprises a chute and a screen extending across said chute.

* * * * *